US00PP27368P3

(12) United States Plant Patent
Moors

(10) Patent No.: US PP27,368 P3
(45) Date of Patent: Nov. 15, 2016

(54) APPLE TREE NAMED 'MORED'

(50) Latin Name: *Malus domestica*
Varietal Denomination: MORED

(71) Applicant: CULTURA JEAN MOORS B.V.B.A, Bilzen (BE)

(72) Inventor: Jozef Jan Moors, Bilzen (BE)

(73) Assignee: Cultura Jean Moors B.V.B.A., Bilzen (BE)

( * ) Notice: Subject to any disclaimer, the term of this patent is extended or adjusted under 35 U.S.C. 154(b) by 177 days.

(21) Appl. No.: 13/998,881

(22) Filed: Dec. 18, 2013

(65) Prior Publication Data

US 2015/0173264 P1 Jun. 18, 2015

(51) Int. Cl.
*A01H 5/08* (2006.01)

(52) U.S. Cl.
USPC ..... Plt./161

(58) Field of Classification Search
USPC ..... Plt./161
CPC ..... A01H 5/0876
See application file for complete search history.

(56) References Cited

PUBLICATIONS

GTITM UPOVROM Citation for 'Mored' as per QZ PBR 20090473; Mar. 16, 2009; 1 page.*
Printout of application information from Community Plant Variety Office (CPVO) website for corresponding CPVO application No. 2009/0473 filed Mar. 16, 2009 (1 page) (http://www.cpvoextranet.cpvo.europa.eu).

* cited by examiner

*Primary Examiner* — Kent L Bell
(74) *Attorney, Agent, or Firm* — Foley & Lardner LLP

(57) ABSTRACT

A new and distinct *Malus domestica* apple tree variety named 'MORED', particularly characterized by a full red or nearly full red fruit skin; very sweet fruit with little acidity; large, juicy and crispy fruit; a productive tree with a high percentage of well-colored fruits that can be picked at the same time; a mid-season time of maturation; and tolerance to mildew.

5 Drawing Sheets

Latin name of the genus and species of the plant claimed: *Malus domestica.*

Variety denomination: 'MORED'.

BACKGROUND OF THE INVENTION

The present invention relates to a new and distinct variety of Apple tree, botanically known as *Malus domestica* of the Rosaceae family, and hereinafter referred to by the variety denomination 'MORED'.

The new *Malus* variety was discovered and selected by the inventor, Jozef Jan Moors, growing in a cultivated area in 1999 in Bilzen, Belgium. The new *Malus* variety was selected by the inventor based on its high productivity, its mid-season time of harvest, and its sweet, large, crispy and juicy fruits that possess little acidity and that have a skin color that is full to nearly full red.

Asexual reproduction of the new *Malus* variety by grafting onto M9 rootstocks was first performed in 2000 in Bilzen, Belgium, and has demonstrated that the combination of characteristics as herein disclosed for the new variety are firmly fixed and retained through successive generations of asexual reproduction. The new variety asexually reproduces true to type.

BRIEF DESCRIPTION OF THE INVENTION

The following traits have been repeatedly observed and are determined to be unique characteristics of 'MORED' which in combination distinguish this Apple tree as a new and distinct variety:

1. full red or nearly full red fruit skin;
2. very sweet fruits with little acidity;
3. large, juicy and crispy fruits;
4. productive tree;
5. high percentage of well-colored fruits that can be picked at the same time;
6. mid-season time of maturation;
7. tolerance to mildew.

Of the many commercial varieties known to the present inventor, the most similar in comparison to the new *Malus* variety 'MORED' is the *Malus* variety 'Red Delicious' (not patented), in the following characteristics described in Table 1:

TABLE 1

Comparison with Similar Variety

| Characteristic | New Variety 'MORED' | Comparison Variety 'RED DELICIOUS' (unpatented) |
|---|---|---|
| Fruit Size | Large | Large |
| Fruit color | Full to nearly full red | Full deep red |
| Fruit shape | Conic to globose-conic | Conic to oblong-conic (cylindrical) |
| Fruit taste | Sweet with little acidity, juicy and crispy | Sweet with little acidity, moderately juicy and not crispy |
| Harvest time | End of September to early October | End of September to early October |

BRIEF DESCRIPTION OF THE PHOTOGRAPHS

The accompanying photographs illustrate the overall appearance of the new *Malus* variety 'MORED' showing the colors as true as is reasonably possible with colored reproductions of this type. Colors in the photographs may differ slightly from the color values cited in the detailed botanical description, which accurately describe the color of 'MORED'.

DETAILED BOTANICAL DESCRIPTION

Figure 1:
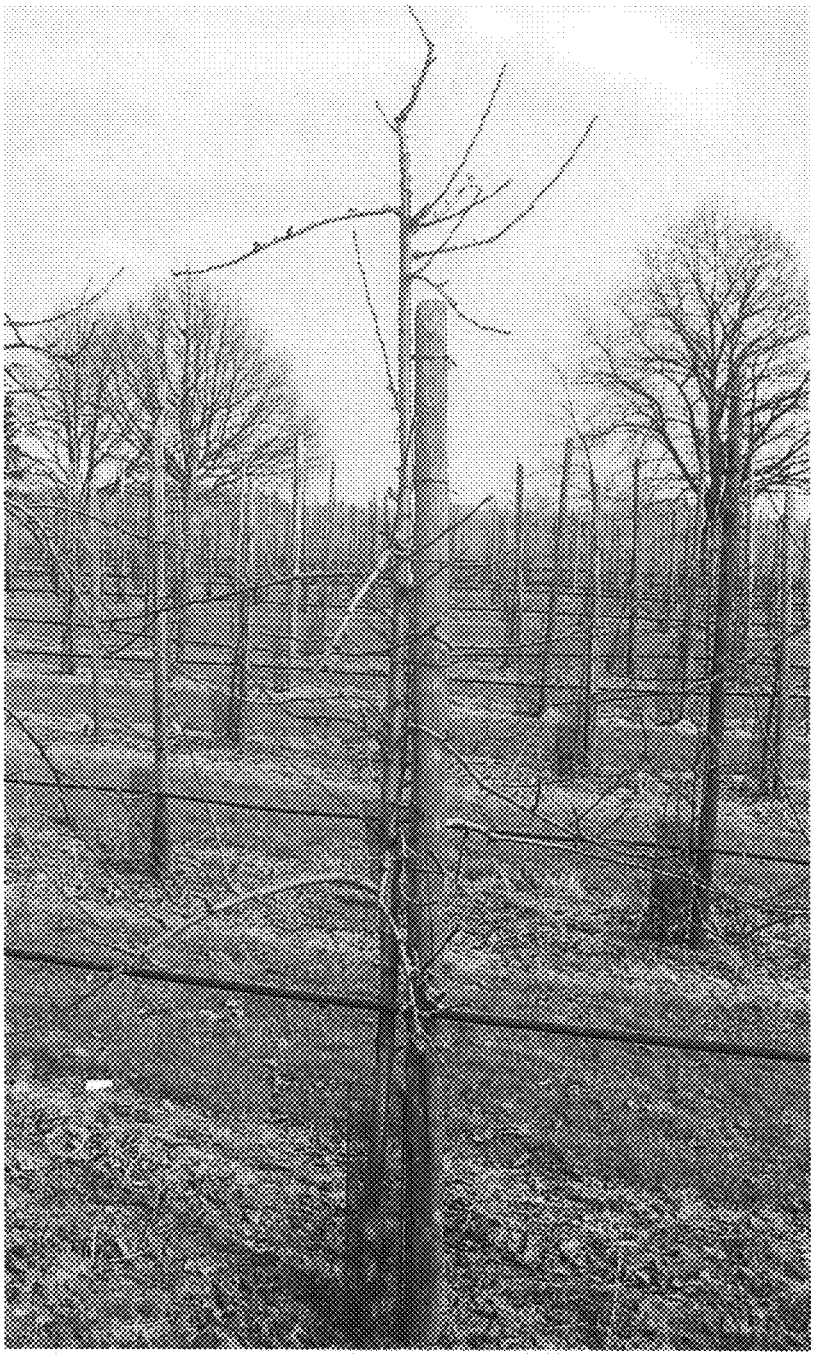
FIG. 1 shows a dormant tree of 'MORED', in the 6$^{th}$ year after planting.
Figure 2:
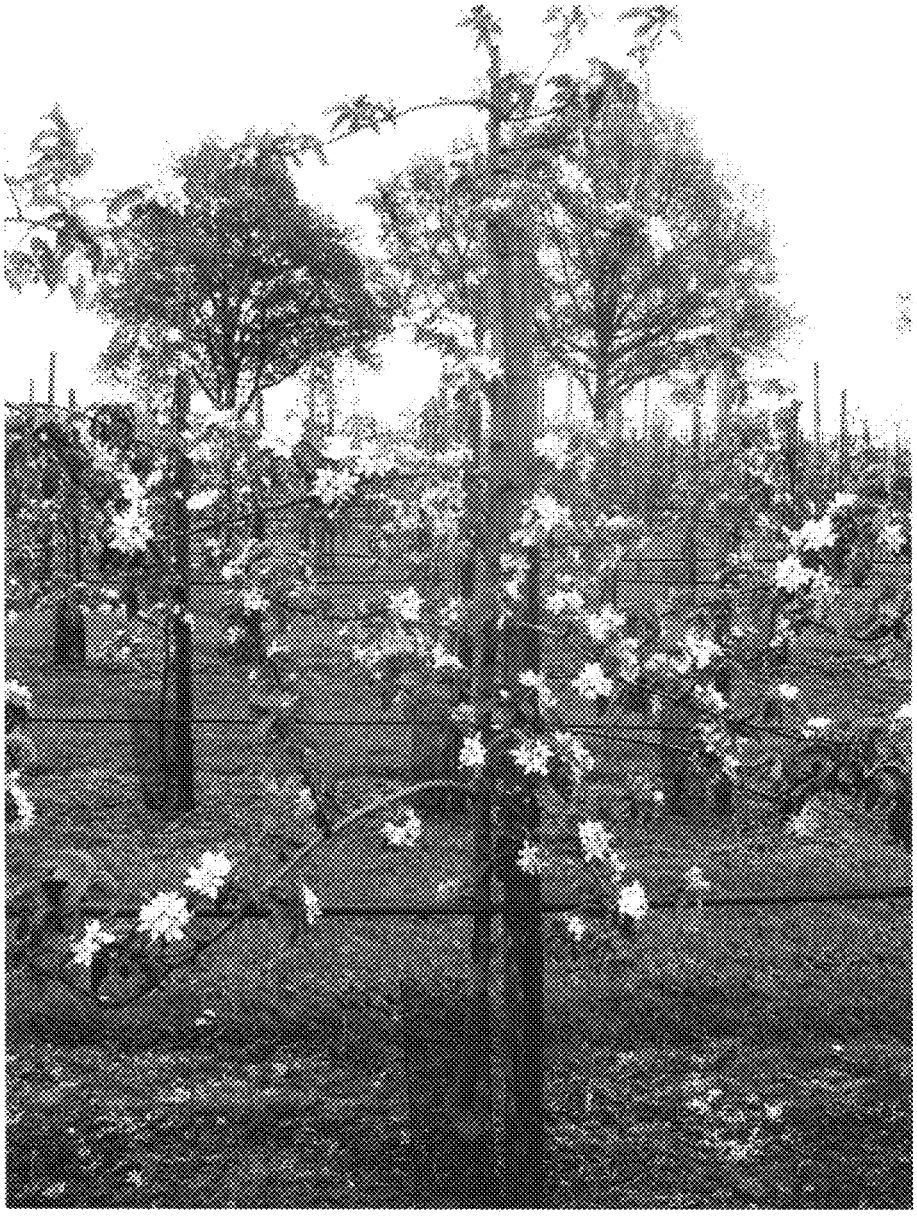
FIG. 2 shows a blooming tree of 'MORED' in the 6$^{th}$ year after planting.
Figure 3:
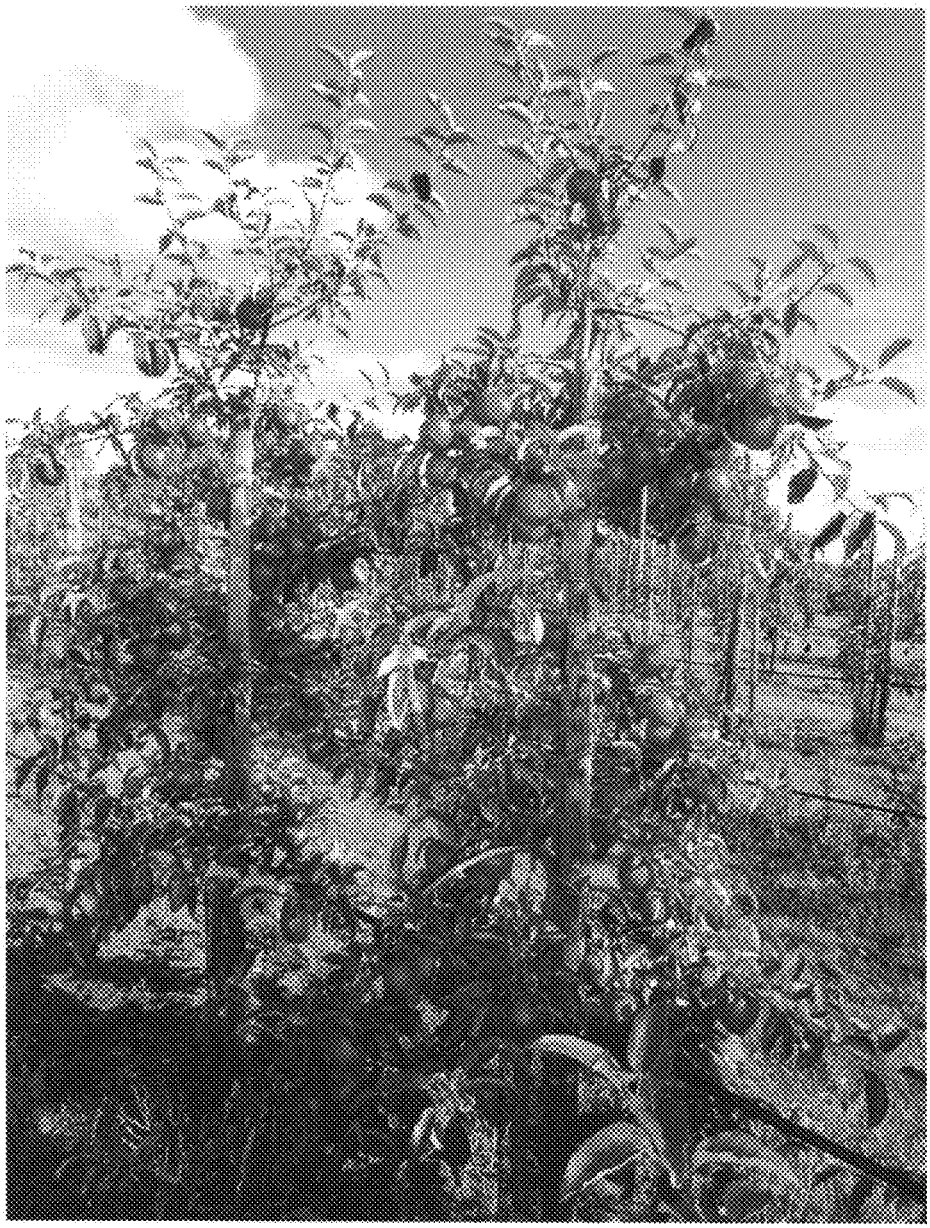
FIG. 3 shows a fruit-bearing tree of 'MORED' in the 5$^{th}$ year after planting.
Figure 4:
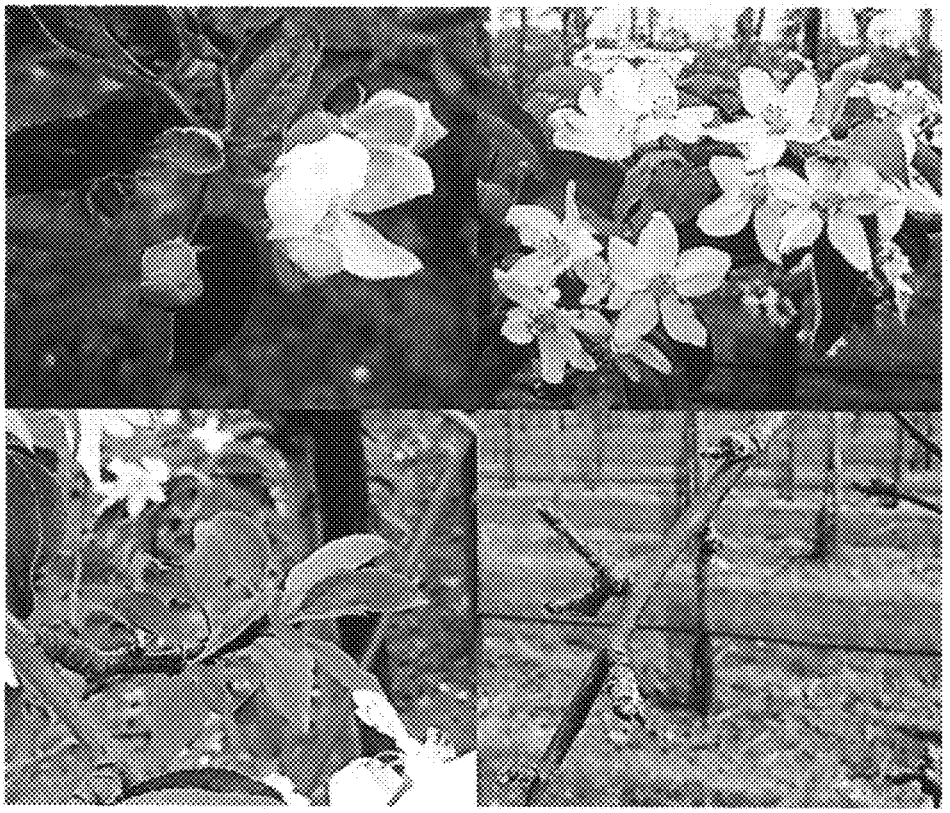
FIG. 4 shows different images of 'MORED' in the 6$^{th}$ year after planting: inflorescences at early flowering (upper left), inflorescences at late flowering (upper right), young leaves (lower left) and dormant buds (lower right).
Figure 5:
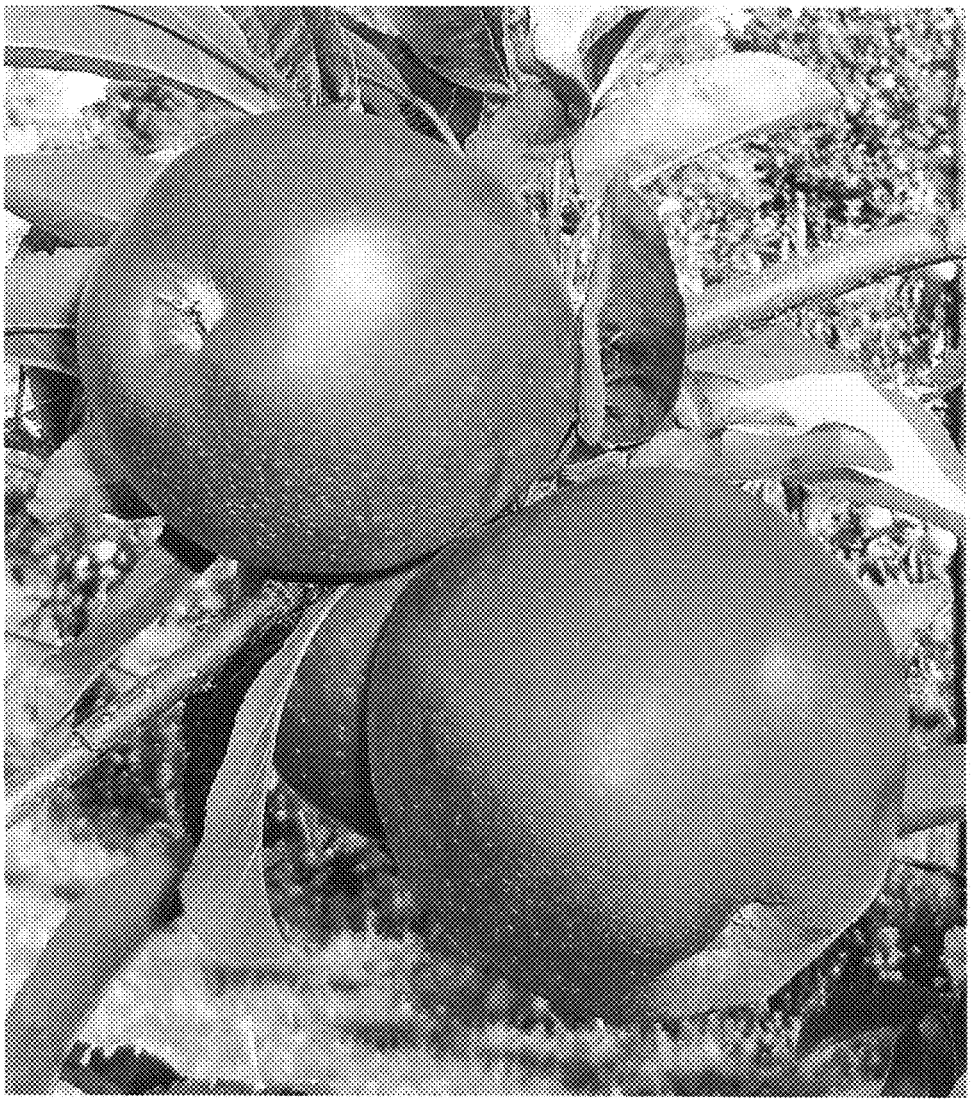
FIG. 5 shows a close-up view of mature fruit of 'MORED' on the tree in the 5$^{th}$ year after planting.

The new *Malus* variety 'MORED' has not been observed under all possible environmental conditions. The phenotype of the new variety may vary with variations in environment such as temperature, light intensity, and day length without any change in the genotype of the Apple tree.

The aforementioned photographs, together with the following observations, measurements and values describe trees of 'MORED' as grown in the field in Sint-Truiden, Belgium, under conditions which closely approximate those generally used in commercial practice.

Trees were spaced 3.0×1.25 m and fertilized with 30 kg/ha of N, 20 kg/ha of $P_2O_5$, 30 kg/ha of $K_2O$ and 50 kg/ha of MgO. The climate is maritime temperate with an average annual rainfall of 852 mm.

Unless otherwise stated, the detailed botanical description includes observations, measurements and values based on 6 year old 'MORED' trees grown in Sint-Truiden, Belgium from 2008 to 2013. Quantified measurements are expressed as an average of measurements taken from a number of trees of 'MORED'. The measurements of any individual tree, or any group of trees, of the new variety may vary from the stated average.

Color references are made to The Royal Horticultural Society Colour Chart (R.H.S.), 2007, except where general colors of ordinary significance are used. Color values were taken under daylight conditions at approximately 3 pm in Sint-Truiden, Belgium.

All of the trees of 'MORED', insofar as they have been observed, have been identical in all the characteristics described below.

Classification:

*Botanical.*—*Malus domestica.*

*Variety denomination.*—MORED.

Parentage:

*Female or seed parent.*—Unknown.

*Male or pollen parent.*—Unknown.

Propagation: Bench-grafting to M9 rootstocks.

Growing conditions:

*Light intensities.*—Full sunlight.

*Temperature.*—During day, grown in the range of 3° C. to 21° C. (monthly average), and during the night, grow in the range of −1° C. to 10° C. (monthly average).

*Fertilization.*—30 kg/ha of N, 20 kg/ha of $P_2O_5$, 30 kg/ha of $K_2O$ and 50 kg/ha of MgO.

*Growth regulators.*—None.

*Pruning or trimming requirements.*—No specific requirements.

Tree:

*Age.*—Observed trees were 5 to 6 years old.

*Vigor.*—Moderate vigor.

*Form.*—Ramified, spreading.

*Habit.*—A large-sized tree with one trunk and 1 leader; main branches spreading; crown symmetrical and pyramidal in shape.

*Branching habit.*—Main branches angle is 80° to 100° with respect to trunk if allowed to grow naturally.

*Density.*—About 2200 trees/ha.

*Cropping behavior.*—Early onset of production; high productivity and average to high amount of flowers; tendency towards biannual bearing if flowers insufficiently thinned.

*Type of bearing.*—On long shoots and spurs.

*Production* (5$^{th}$ *year*).—About 20 kg/tree.

*Size at maturity.*—Height: About 2.5 m. Spread: About 2.0 m (at the level of the lower branches).

*Trunk.*—Height (up to the first branches): About 0.70 m. Diameter: About 40 mm at 20 cm above the graft union. Texture: Smooth with numerous lenticels, shallow furrows. Bark color: Primarily RHS 202C with RHS 199A, under bark. Trunk Lenticels: Length: About 2 mm. Width: About 1 mm. Color: RHS N199C. Density: About 3.8 per cm$^2$.

*Branches.*—Number per tree: About 20. Length: Varies due to shape of tree; maximum of 70 cm to 100 cm; minimum of 15 cm to 30 cm. Diameter: About 10 mm to 15 mm. Surface texture: Smooth. Pubescence: No. Color: Mature (after about 5 years): RHS 200C. New Growth: RHS 187A. Internode length: About 2 cm to 5 cm. Internode diameter: About 4 mm to 5 mm. Branch lenticels: Length: About 1 mm. Width: About 1 mm. Color: RHS 163B. Density: About 8 per cm$^2$.

*Spur.*—Present: Yes. Distance between each spur: On the 3 to 5 year old branches, the distance is about 40 mm. Diameter of each spur: About 8 to 11 mm. Average number of fruit per fruit-bearing spur: About 1.6.

Foliage:

*Arrangement.*—Alternate.

*Lamina.*—Size: Length: About 100 mm (fully expanded leaf). Width: About 50 mm (fully expanded leaf). Length/width ratio: 2.0. Overall Shape: Ovate, petiolated. Base shape: Rounded. Apex shape: Acute. Margin: Serrate. Texture: Upper surface: Glabrous. Under surface: With weak pubescence. Attitude in relation to shoot: Outwards. Color (mature leaves): Upper surface: RHS 136A. Under surface: RHS 137C. Color (immature leaves): Upper surface: RHS 137A. Under surface: RHS 137C.

*Venation*.—Type: Pinnate. Color: RHS 137C.

*Petiole*.—Length: About 30 mm. Diameter: About 2 mm. Texture: Light pubescence. Color: RHS 137C.

*Stipule*.—Arrangement: Adnate. Length (distance of stipules from basal attachment of petiole): About 4 mm to 6 mm. Width: About 0.5 mm to 1.0 mm.

Inflorescence:

*Blooming time*.—Full bloom on about April 27$^{th}$ (average over a 5-year period), similar to 'Golden Delicious'.

*Blooming period*.—About 12 to 14 days.

*Fragrance*.—Slight to medium.

*Type*.—Cyme.

*Number of flowers per inflorescence*.—About 4 to 6.

*Inflorescence size*.—Diameter: About 8.0 cm. Depth: About 4.7 cm.

*Buds*.—Number per spur: About 1 per spur. Length: About 10 mm. Width: About 5 mm. Texture: fairly strong pubescence. Color: Apex, RHS 166A and base, RHS 181A. Scales: Number: About 7 to 10. Color: Upper: RHS 166A. Lower: RHS 181A.

*Petals* (*open flower stage*).—Arrangement: Intermediate to overlapping. Number per flower: Five. Size: Length: About 27 mm. Width: About 16 mm. Length/width ratio: 1.69. Overall shape: Ovate. Apex shape: Obtuse. Base shape: Oblique. Texture (upper surface): Smooth. Texture (lower surface): Smooth. Margin: Entire. Color (upper surface): Hue of pink (RHS 70C) fading to white. Color (lower surface): Streaks of pink (RHS 70C) on white.

*Sepals*.—Number per flower: Five. Size: Length: About 12.3 mm. Width: About 3.5 mm. Length/width ratio: 3.5. Overall shape: Triangular. Apex shape: Acute. Base shape: Truncate. Texture (upper surface): Mild pubescence. Texture (lower surface): Strong pubescence. Margin: Entire. Color (upper surface): Apex, RHS 64D, and base, RHS 145A. Color (lower surface): Apex, RHS 64D, and base, RHS 145A.

*Pedicel*.—Length: 24 to 27 mm. Diameter: 2 to 3 mm. Texture: Tomentose, color of hairs RHS N155A. Color: RHS 139C.

Fruit:

*Keeping quality*.—The fruit keeps well on the tree. It can be stored in cold temperature conditions (non-controlled atmosphere) for up to 4 months without losing firmness and juiciness. Under ULO (ultra-low oxygen) conditions the fruit can be stored for at least 10 months. It has a shelf life up to 10 days without losing firmness and juiciness.

*Maturity when described*.—Ripe for eating.

*Maturity period after full bloom*.—About 152 days after full bloom on April 27$^{th}$

*Date of first and last picking* (*harvest*).—September 25$^{th}$ and October 5$^{th}$ in Sint-Truiden, Belgium (North 50.77076°, East 5.159966°) in the year 2012.

*Type*.—Pome.

*General shape*.—Conic to oblong-conic.

*Average weight*.—About 222 g.

*Fruit size*.—Average height: About 74 mm. Average diameter (at widest point): About 79 mm. Position of maximum diameter: At 53% of height near stem end. Height/thickness ratio: 0.94.

*Stem*.—Length: About 27 mm. Diameter: About 2 mm. Color: RHS N77A.

*Stalk cavity*.—Depth: About 18 mm. Width: About 35 mm.

*Eye basin*.—Depth: About 11 mm. Width: About 28 mm. Crowning at calyx end: Moderate. Position of sepals: Half-closed.

*Skin*.—Thickness: Thin. Texture: Smooth. Bloom: Faint. Greasiness: Absent. Firmness (at picking time): 7.5 to 8.5 kg/cm$^2$. Over color Color: RHS 53A. Percentage of skin surface with overcolor color: About 80 to 100%. Pattern of overcolor: Solid flush. Intensity of over color: High. Ground color: RHS 2C. Skin Lenticels: Length: About 1 mm. Width: About 1 mm. Color: RHS N155D. Density: About 8 per cm$^2$.

*Flesh*.—Color: RHS 2D. Texture: Fine, crispy and juicy. Aroma: Faint. Eating quality: Very good with very high level of sugar and low level of acids. Sugar content (at picking time): 14 to 16° Brix. Starch content (at picking time): 6-7 (iodine index). Acidity (at picking time): 1.5 to 2.4 g/l. Core: Symmetry of core: Symmetrical. Distinctness of core lines: Faint. Locules: Number (per fruit): 5. Length: About 14 mm. Width: About 10 mm. Form: Partly open.

Seeds:

*Number per fruit*.—About 3 to 10.

*Number per locule*.—About 1 to 2.

*Shape*.—Ellipsoid and pointed.

*Length*.—About 8 mm.

*Width*.—About 5 mm.

*Texture*.—Smooth.

*Color*.—RHS 165A.

Reproductive organs:

*Androecium*.—Stamen: Number per flower: 20. Length: About 5 to 8 mm. Color: RHS 8C. Anther: Length: About 2.5 mm. Color: RHS 8C. Filaments: Length: About 3 to 5 mm. Color: RHS 157B. Pollen: Amount: Moderate. Color: RHS 8C. Pollinators Requirements: Good pollinators are, for example, 'Golden Delicious' and 'Golden Gem'.

*Gynoecium*.—Pistils: Quantity: 5. Length: About 7 mm. Color: RHS 145A. Stigmas: Length: About 0.5 mm. Width: About 0.5 to 1 mm. Color: RHS 145A. Ovary: Length: About 4 mm. Width: About 3 mm. Color: RHS 53C.

Use: Fresh market.

Disease/pest resistance: Low susceptibility for apple canker (*Neonectria galligena*), tolerance to mildew (*Podosphaera leucotricha*) and *Gloeosporium* rot.

Disease/pest susceptibility: Susceptible to apple scab (*Venturia inequalis*).

Winter hardiness: Tolerant to temperatures down to −20° C. without observed damage to wood and buds of dormant apple trees.

Drought/heat tolerance: Tolerant to temperatures up to minimal 35° C., growth is limited by drought periods without irrigation.

Shipping/storage characteristics: Low sensitivity to bruising. Fruit can be stored in cold temperature conditions (non-controlled atmosphere) for up to 4 months without losing firmness and juiciness. Under ULO (ultra-low oxygen) conditions the fruit can be stored for at least 10 months.

The invention claimed is:

1. A new and distinct variety of *Malus domestica* apple tree named 'MORED', as illustrated and described herein.

* * * * *